United States Patent
Kim et al.

(10) Patent No.: US 6,534,270 B2
(45) Date of Patent: Mar. 18, 2003

(54) BIOCHIP AND METHOD FOR FABRICATING THE SAME

(75) Inventors: Su Hyeon Kim, Seoul (KR); Je Kyun Park, Seoul (KR); Tae Han Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 09/832,944

(22) Filed: Apr. 12, 2001

(65) Prior Publication Data

US 2001/0031504 A1 Oct. 18, 2001

(30) Foreign Application Priority Data

Apr. 14, 2000 (KR) ......................................... 2000-19583

(51) Int. Cl.[7] ...................... G01N 33/53; G01N 33/543; B05D 3/00; B05D 3/12
(52) U.S. Cl. ................ 435/6; 435/4; 435/7.1; 435/7.92; 435/174; 435/176; 435/177; 435/961; 435/969; 436/518; 436/524; 436/527; 436/528; 436/529; 436/530; 436/174; 436/807; 436/809; 436/823; 427/2.11; 427/2.13; 427/8; 427/162; 427/163.1; 427/163.2; 427/177; 427/180; 427/289; 427/331; 427/355; 427/356; 427/430.1
(58) Field of Search ..................... 435/4, 6, 7.1, 7.92, 435/174, 176, 177, 961, 969; 436/518, 524, 527–530, 174, 807, 809, 823; 427/2.11, 2.13, 8, 9, 10, 162, 163.1, 163.2, 177, 180, 289, 331, 355, 356, 430.1

(56) References Cited

U.S. PATENT DOCUMENTS

| 5,730,933 A | * | 3/1998 | Peterson | ...................... 422/22 |
| 6,037,186 A | * | 3/2000 | Stimpson | ..................... 436/518 |
| 6,129,896 A | * | 10/2000 | Noonan et al. | ........... 422/82.05 |

FOREIGN PATENT DOCUMENTS

WO     WO 99/03341 A1  *  1/1999

* cited by examiner

*Primary Examiner*—Long V. Le
*Assistant Examiner*—Kartic Padmanabhan
(74) *Attorney, Agent, or Firm*—Fleshner & Kim, LLP

(57) ABSTRACT

Disclosed are biochips having a high detecting sensitivity with readiness in fabrication of microarray, and a method for fabricating the same, in which a solid support wound with fibers is immersed in a solution containing biomolecules to immobilize the biomolecules onto the fiber, and the individual fibers with the biomolecules immobilized thereon are straightened and arranged. The arranged fibers are embedded with a defined material and cut in a direction perpendicular to the lengthwise arrangement direction of the fibers to obtain thin chips. The chips are placed on a substrate to remove the material used for embedding and thereby remain fibers with the immobilized biomolecules on the substrate. This biochip fabrication method immobilizes a great number of biomolecules onto the fibers having a large surface area to enhance the detection sensitivity and allows production of a great number of substrates with an array of biomolecules immobilized simultaneously.

17 Claims, 5 Drawing Sheets fiber with immobilized biomolecules fiber with immobilized biomolecules fiber with immobilized biomolecules embedded array of fibers fiber with immobilized biomolecules biomolecule fiber fragment with immobilized biomolecules

BIOCHIP AND METHOD FOR FABRICATING THE SAME

BACKGROUND OF THE INVENTION

1. Field of the Invention

The present invention relates to a method for fabricating biochips and, more particularly, to a method for fabricating a plurality of microarrays.

2. Description of the Related Art

Non-covalent bonds such as ionic bond, hydrogen bond and Van der Waals bond in an aqueous solution are generally about 30 to 3000 times as weak as the covalent bond and hardly stable in the aqueous solution. However, macromolecules have so many bonding sites to maintain stable bonding at the room temperature.

The non-covalent bonds contribute to very selective detection and identification of a specific molecule.

Such a molecule that can recognize specific molecules from the other molecules is broadly defined as "receptor", the examples of which include membrane proteins taking charge of signal transmission from the surface of the cell into the cell membrane, oligonucleotides or peptide nucleic acids (PNAs) recognizing the specific sequence of DNA, antibodies involving the immune mechanism, enzymes hydrolyzing metabolites, and the like.

A substance that selectively binds to these receptors is referred to as "ligand".

In 1975, Edwin Southern developed the Southern blotting analysis, an approach for detection and identification of a DNA having a specific base sequence. In the Southern blotting analysis, DNA fragments are separated by size in the electrophoresis and moved on a solid substrate such as a nitrocellulose or nylon membrane so that the relative positions of the DNA fragments are maintained.

Subsequently, DNA or RNA having a specific base sequence labeled with a radioactive isotope is placed as a probe into the DNA fragments immobilized on the solid substrate.

The DNA or RNA placed as a probe can bind to the DNA fragments that have a complementary sequence by way of hybridization, which allows identification of the position of the DNA having a specific base sequence.

This approach has been extended to the Northern blotting analysis for analyzing RNA using RNA-DNA hybridization, and the Western blotting analysis for antibody-based protein analysis, all of the blotting analyses are based on the molecular selectivity of biological macromolecules with non-covalent bonds between the receptor and the ligand.

In addition, ELISA (Enzyme-Linked Immunosorbent Assay), which is one of the analysis methods using an antibody like Western blotting analysis, is most widely used in many applications including molecular biology, medical diagnosis, environmental analysis, etc.

These many analysis methods using receptor-ligand bonds are in most cases concerned to the limited number of receptors and ligands.

For example, at least about 1,000,000 DNA molecules of much various structures are available in fabricating a DNA having a sequence of 10 bases from four bases.

Therefore, the experiments concerning the binding reaction between receptors and ligands require repeating procedures with enormous labor, time and resources.

To solve the problem, biochip technologies have been developed, which have the form of microarray in which a plurality of receptors or ligands are two-dimensionally arranged at known positions on the substrate. Such biochips are divided, depending on the type of the biomolecule, into DNA chips using DNA probes, protein chips using proteins such as enzyme or antigen/antibody, and cell chips using cells.

In the fabrication method of microarray for oligonucleotide or peptide chips, the biomolecules can be directly synthesized on the substrate in the chips. However in the most cases, the previously synthesized or purified biomolecules are placed on the substrate as the biologically important molecules such as cDNA or proteins are difficult to be synthesized on the substrate. The method involving direct synthesis of the biomolecules on the substrate provides highly integrated microarrays but requires a complicated fabrication process at high cost. The method of placing the synthesized or purified biomolecules on the substrate typically uses pin-based microspotting technologies, which is disadvantageous in large-scaled production.

SUMMARY OF THE INVENTION

It is, therefore, an object of the present invention to provide biochips having a high detecting sensitivity with readiness in fabrication of microarray, and a method for fabricating the same.

To achieve the above object of the present invention, there is provided a method for fabricating biochips including the steps of: (a) immersing fibers wound on solid supports in a solution containing biomolecules to absorb and immobilize the biomolecules onto the fibers; (b) arranging the individual fibers with the biomolecules immobilized thereon, the fibers being separated from each other at a predetermined distance; (c) embedding the arranged fibers with a defined material; (d) cutting the embedded fibers in a direction perpendicular to the lengthwise arrangement direction of the fibers to obtain thin chips; and (e) placing the chips on a substrate and removing the defined material used to embed the fibers, thereby remaining the fiber fragments with the immobilized biomolecules on the substrate.

The fibers are embedded with a wax, ice, or polymer material, and the substrate is a solid substrate.

In another aspect of the present invention, there is provided a biochip including: fibers with biomolecules immobilized thereon; a solid polymer or a frozen aqueous solution filled between the fibers, the fibers being arranged and separated from each other at a predetermined distance.

In another aspect of the present invention, there is provided a biochip including fibers with biomolecules immobilized thereon, the fibers being arranged and separated from each other at a predetermined distance.

Other objects, features and advantages of the present invention will become evident in the detailed description with reference to the following accompanying drawings.

DETAILED DESCRIPTION OF THE PREFERRED EMBODIMENT

Hereinafter, the present invention will be described in detail by way of the following examples and experimental examples, which are not intended to limit the scope of the present invention.

Figure 1A:
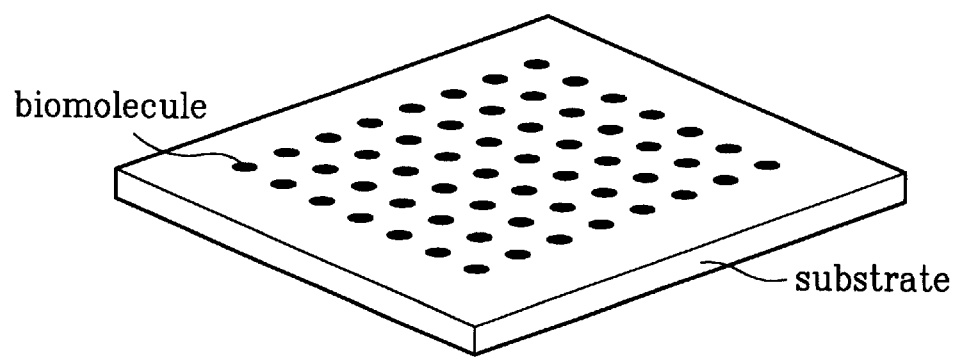
FIGS. 1a and 1b are illustrations of array of fiber fragments immobilized on a substrate in biochips according to the present invention.
Figure 1B:
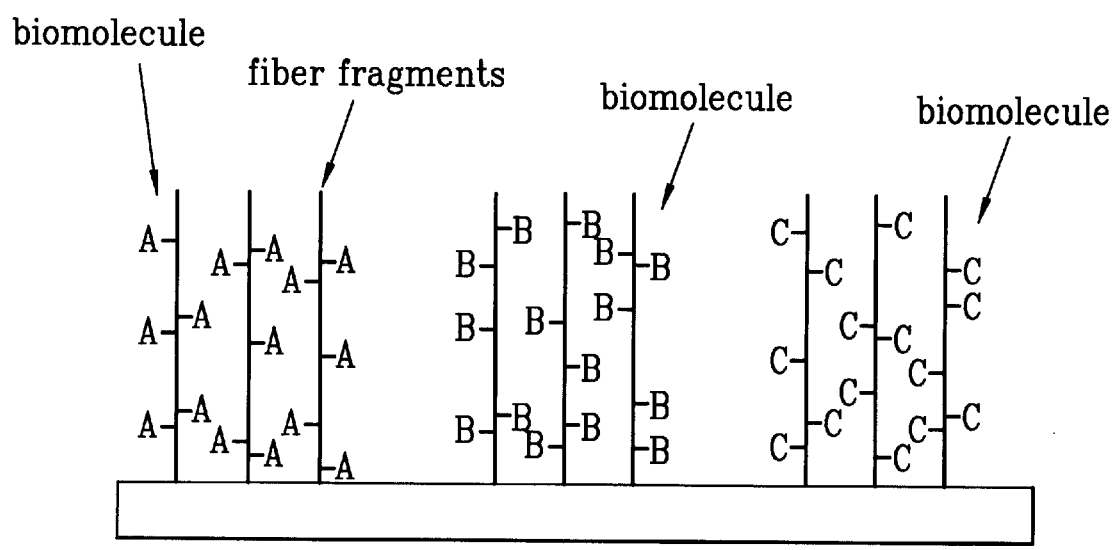

FIGS. 1a and 1b are illustrations of array of fiber fragments placed on a substrate, with biomolecules immobilized on the fibers in accordance with the present invention.

As shown in FIGS. 1a and 1b, fiber fragments with biomolecules arranged in a biochip structure having a two-dimensional form are immobilized on the surface of the substrate, different biomolecules being immobilized in different sites on the surface of the substrate.

FIGS. 2a to 2g are perspective views showing a method for fabricating biochips according to the present invention.

Figure 2A:
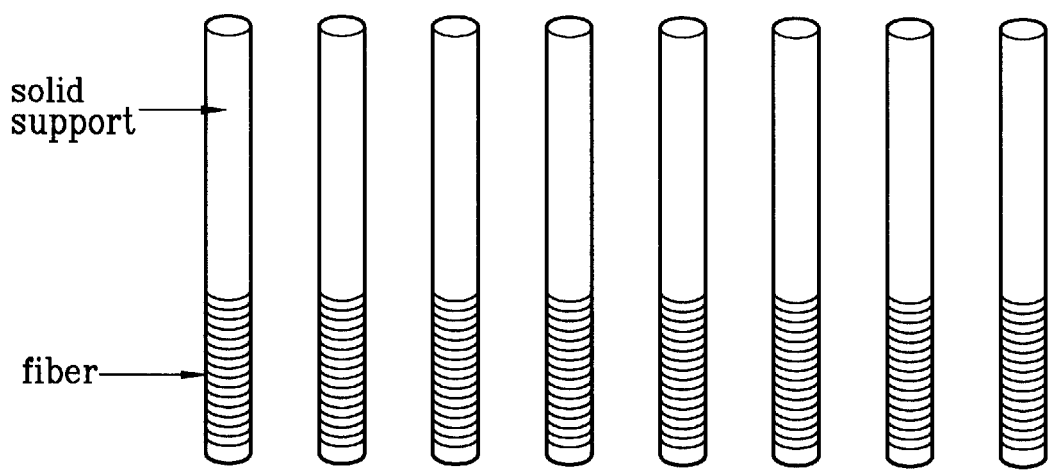
FIGS. 2a to 2g are perspective views showing a method for fabricating biochips according to the present invention.

First, as shown in FIG. 2a, the fibers are wound round solid supports. The solid supports are cylindrical rods, and the fibers can be natural fibers such as cotton, silk or wool, or synthetic fibers such as nylon, polyethylene, polyester, glass fiber or acrylic fiber. The diameter of the fiber is in the range from 100 nm to 1 mm.

Figure 2B:
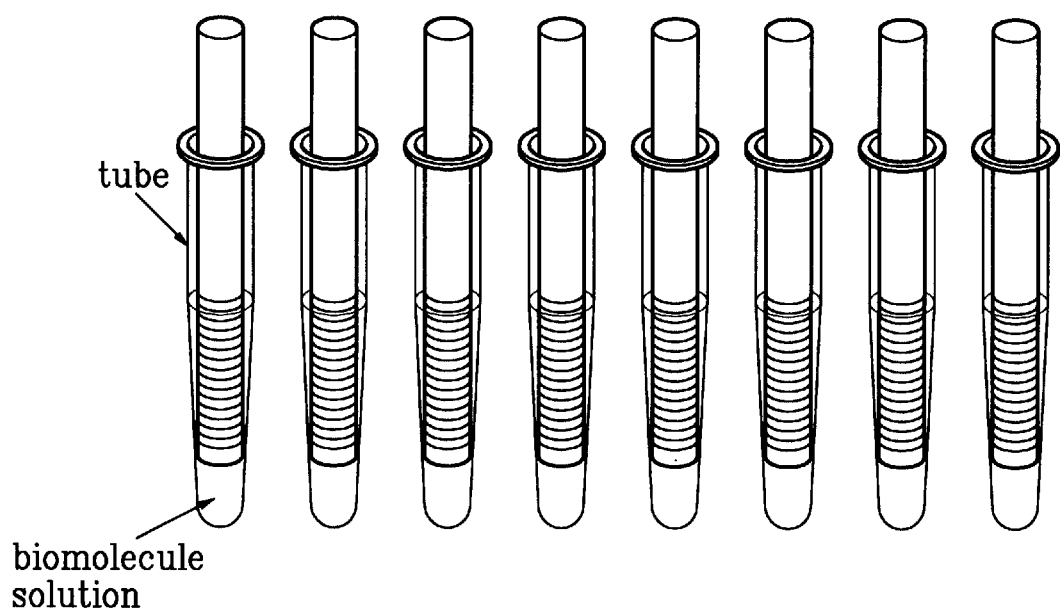

As shown in FIG. 2b, the fibers are immersed in a solution containing biomolecules so that the biomolecules are penetrated and immobilized into the fibrous material. Examples of the biomolecules include DNA, RNA, PNA (Peptide Nucleic Acids), oligonucleotides, peptides, proteins, membranes, polysaccharides, antigen, antibody, physiologically active organic molecules, and the like.

There are two methods for immobilization of the biomolecules into the solid support: physical and chemical methods in which the biomolecules are first penetrated into the fibrous material. The physical method involves physically binding the biomolecules to the fibrous material. In the chemical method, the biomolecules which are penetrated into the fibrous material have functional groups such as carbonyl or amino groups covalently bonded to the fibrous material.

Figure 2C:
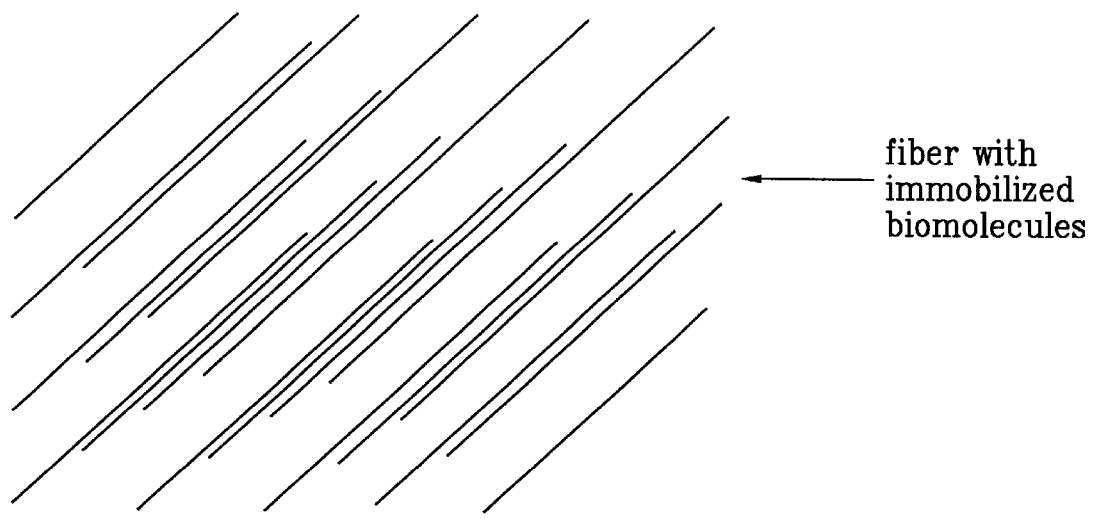

Subsequently, as shown in FIG. 2c, the fibers with the biomolecules immobilized thereon are stretched and arranged at regular intervals. The distance between the fibers is properly controllable depending on the use of the biochips obtained so as to prevent improper chemical reactions from occurring between the biomolecules and mingling of biomolecules between neighboring fibers.

Figure 2D:
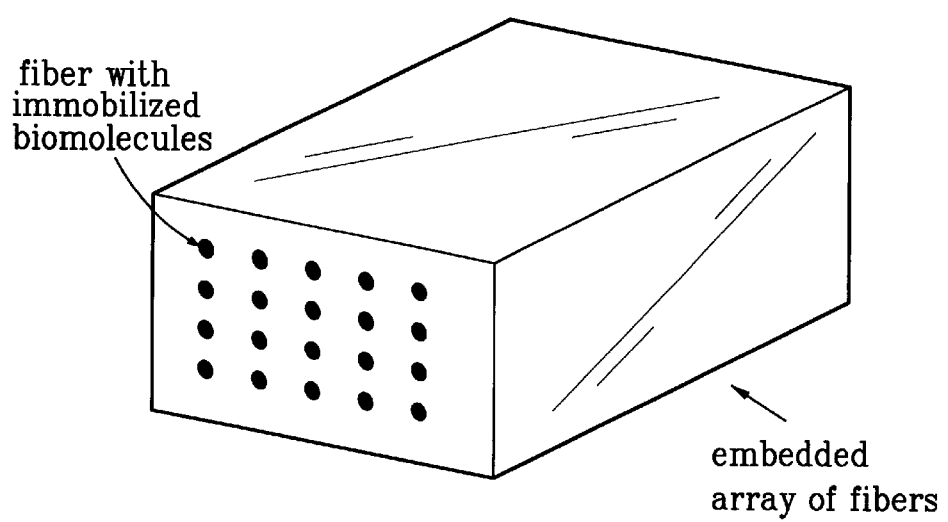

As shown in FIG. 2d, the arranged fibers are embedded with a wax or polymer material. The wax may include paraffin. Examples of the polymer material include epoxy, methyl methacrylate, glycol methacrylate, etc.

The embedding process may use an aqueous solution instead of the wax or polymer material. In this case, a bundle of the fibers are immersed in the aqueous solution and then frozen.

Figure 2E:
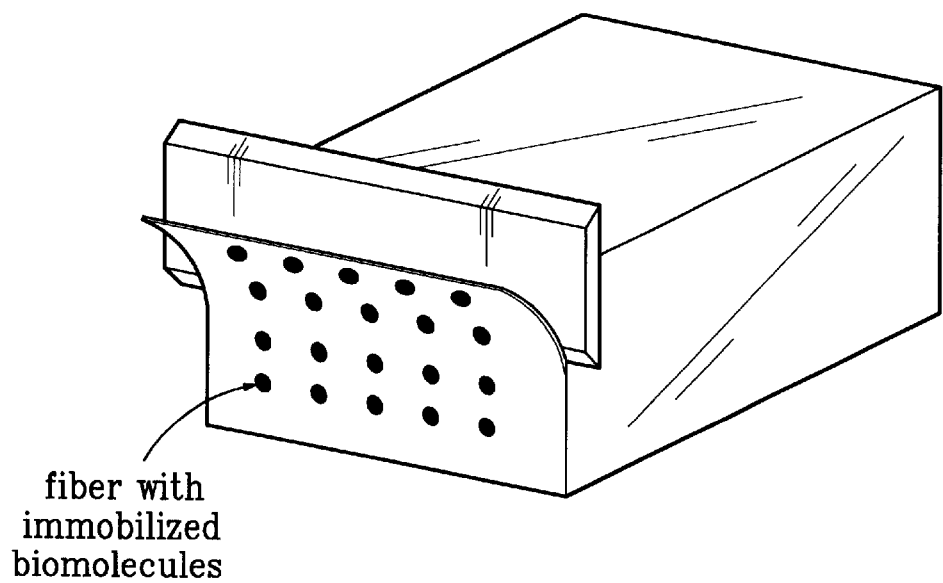

As shown in FIG. 2e, the fibers embedded with a wax or polymer material are cut into thin chips in a direction perpendicular to the lengthwise direction of the fibers arranged.

The embedded fibers are cut with a microtome or ultra-microtome into thin chips having a thickness of 10 nm to 100 $\mu$m.

The thin chips are arranged in the same manner as the fibers onto which different biomolecules are immobilized, so that different biomolecules are two-dimensionally arranged at regular intervals on the chips.

Figure 2F:
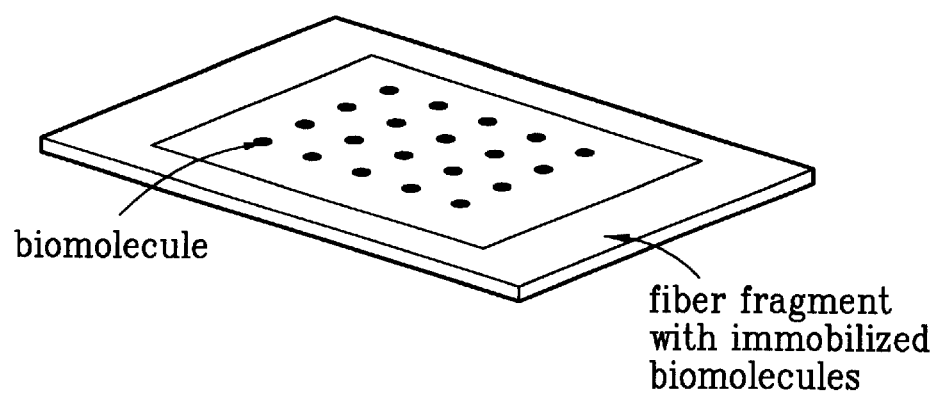

As shown in FIG. 2f, the thin chips are placed on the substrate, which is a solid substrate and gives mechanical strength to the thin chip. The solid substrate may include a slide glass, silicon, and a polymer substrate such as, polycarbonate, polystyrene, polyethylene, or acryl-based polymer. The substrate placed with the fibers embedded chip can be used to identify the biomolecules as it is. But to increase accessibility of sample solution the embedding material, wax, polymer or ice, can be removed.

Figure 2G:
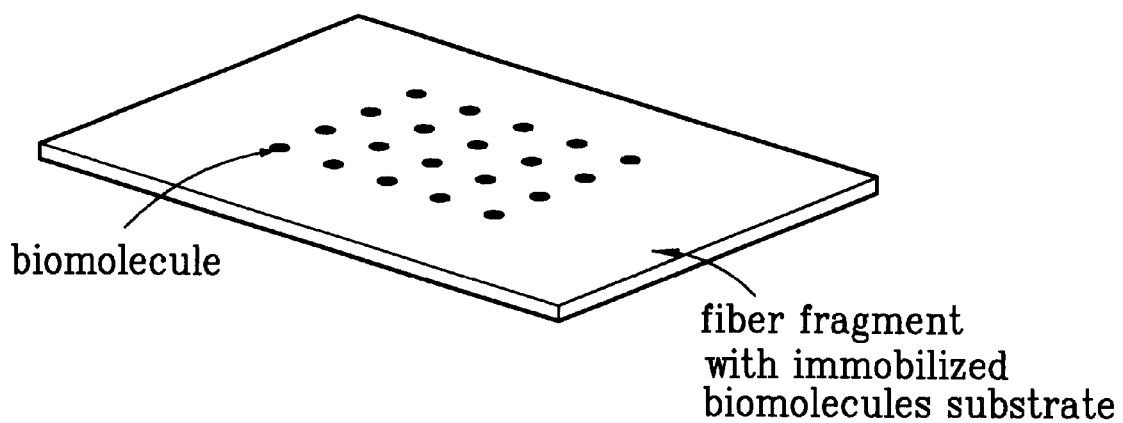

That is, as shown in FIG. 2g, the paraffin wax or the polymer material used to embed the fibers for the purpose of fixing fibers is dissolved in a solvent and removed to remain only the array of biomolecules attached to the fiber fragments on the substrate.

In the case when the fibers are embedded in the frozen aqueous solution, raising the temperature and/or reduce pressure can remove embedding material, water, on the substrate.

The method for fabricating biochips according to the present invention as described above has the following effects.

First, when compared with a microarray having biomolecules immobilized onto the surface of the substrate, as a fiber is consist of a bunch of thin fiber filaments, a larger number of biomolecules can be immobilized onto the fiber filaments having a large surface area to enhance the detection sensitivity of the biochips.

Second, a plurality of microarrays can be simultaneously fabricated with an almost uniform quantity of biomolecules being immobilized onto the fibers, thus enhancing the repeatability of the tests.

Third, a large number of biochips, which contain array of biomolecules on supporting substrates, can be produced at a time, that reduce the production cost of the biochips.

Finally, regular interval between the fibers with biomolecules gives several advantages; first, prevent improper chemical reactions that can occur between the biomolecules; second, avoid mingling of biomolecules between neighboring fibers; third, facilitate identification of the biomolecules to be examined.

While this invention has been described in connection with what is presently considered to be the most practical and preferred embodiment, it is to be understood that the invention is not limited to the disclosed embodiments, but, on the contrary, is intended to cover various modifications and equivalent arrangements included within the spirit and scope of the appended claims.

What is claimed is:

1. A method for fabricating biochips, comprising:
   immersing individual fibers wound around solid supports in solution containing biomolecules to immobilize the biomolecules onto the individual fibers;
   arranging the individual fibers with the biomolecules immobilized thereon to be separated from each other by a predetermined distance;
   embedding the arranged fibers within a frozen aqueous material by immersing the arranged fibers in an aqueous solution and freezing the arranged fibers in the aqueous solution;
   cutting the embedded fibers in a direction perpendicular to the lengthwise arrangement direction of the fibers to obtain chips; and
   placing the chips on a substrate and removing the frozen aqueous material used to embed the fibers, wherein the fibers with the immobilized biomolecules on the substrate remain.

2. The method as claimed in claim 1, wherein the biomolecules are selected from the group consisting of DNA, RNA, PNA (Peptide Nucleic Acid), oligonucleotides, peptides, proteins, membranes, polysaccharides, antigens, antibodies and organic biomolecules.

3. The method as claimed in claim 1, wherein the fibers include natural and synthetic fibers.

4. The method as claimed in claim 1, wherein a diameter of the fibers is from about 100 nm to 1 mm.

5. The method as claimed in claim 1, wherein the immersing of the individual fibers in solution comprises immobilizing the biomolecules onto the support by penetrating the biomolecules into the fibers for physical binding between the biomolecules and the fibers.

6. The method as claimed in claim 5, wherein the immersing of the individual fibers in solution comprises immobilizing the biomolecules onto the support by covalently binding the biomolecules to the fibers with a functional group for chemical reactions.

7. The method as claimed in claim 6, wherein the functional group includes a carbonyl or amino group.

8. The method as claimed in claim 1, wherein the cutting of the embedded fibers comprises cutting the embedded fibers with a microtome or an ultramicrotome.

9. The method as claimed in claim 1, wherein the cutting of the embedded fibers comprises cutting the fibers in a direction perpendicular to the lengthwise direction of the fibers into chips, the chips having a thickness of 10 nm to 100 um.

10. The method as claimed in claim 1, wherein the substrate is a solid substrate.

11. The method as claimed in claim 10, wherein the solid substrate comprises a slide glass or a polymer substrate, wherein the polymer substrate is selected from the group consisting of polycarbonate, polystyrene, polyethylene and acryl-based polymer.

12. The method as claimed in claim 1, wherein the individual fibers with the biomolecules are arranged at regular intervals to prevent mingling of biomolecules between neighboring individual fibers and wherein the frozen aqueous material is around and between the individual fibers.

13. The method as claimed in claim 1, wherein only the fibers with the immobilized biomolecules remain on the substrate after the frozen aqueous material is removed.

14. A method for fabricating biochips, comprising:

winding fibers around solid supports;

immersing the fibers and the solid supports in a solution comprising biomolecules;

stretching and arranging the fibers to be separated from each other at predetermined distances;

immersing the arranged fibers in a hardening solution, wherein the hardening solution flows around and between the arranged fibers;

hardening the hardening solution to fix arrangement positions of the fibers, wherein only the hardening solution is holding the fibers in position;

cutting the fibers in the hardened solution in a direction perpendicular to the lengthwise direction of the fibers to form chips;

placing the chips on a substrate; and removing at least part of the hardened solution.

15. The method as claimed in claim 14, wherein all of the hardening solution is removed and only the fibers with the immobilized biomolecules remain on the substrate.

16. The method as claimed in claim 14, wherein the hardening solution is a liquid wax or polymer material that is removed after hardening by dissolving the hardened wax or polymer material in a solvent.

17. The method as claimed in claim 14, wherein the hardening solution is an aqueous solution that is removed after hardening by melting.

* * * * *